(12) United States Patent
Hanna

(10) Patent No.: US 7,384,429 B2
(45) Date of Patent: Jun. 10, 2008

(54) INTRACAPSULAR ACCOMODATIVE IMPLANTS

(75) Inventor: Khalil Hanna, Paris (FR)

(73) Assignee: HumanOptics AG (DE)

( * ) Notice: Subject to any disclaimer, the term of this patent is extended or adjusted under 35 U.S.C. 154(b) by 225 days.

(21) Appl. No.: 10/503,329

(22) PCT Filed: Feb. 3, 2003

(86) PCT No.: PCT/FR03/00320

§ 371 (c)(1), (2), (4) Date: Aug. 2, 2004

(87) PCT Pub. No.: WO03/063738

PCT Pub. Date: Aug. 7, 2003

(65) Prior Publication Data

US 2005/0085906 A1   Apr. 21, 2005

(30) Foreign Application Priority Data

Feb. 1, 2002   (FR)   .................................. 02 01240

(51) Int. Cl.
*A61F 2/16*   (2006.01)

(52) U.S. Cl. ...................................................... 623/6.32

(58) Field of Classification Search ........ 623/6.32–6.37
See application file for complete search history.

(56) References Cited

U.S. PATENT DOCUMENTS

| | | | |
|---|---|---|---|
| 4,556,998 A | 12/1985 | Siepser | |
| 4,710,194 A | 12/1987 | Kelman | |
| 4,878,910 A * | 11/1989 | Koziol et al. | 623/6.38 |
| 4,888,012 A | 12/1989 | Horn et al. | |
| 5,066,301 A | 11/1991 | Wiley | |
| 5,135,592 A | 8/1992 | Melvin | |
| 6,051,024 A * | 4/2000 | Cumming | 623/6.44 |
| 6,113,633 A * | 9/2000 | Portney | 623/6.32 |
| 6,638,305 B2 * | 10/2003 | Laguette | 623/6.37 |

FOREIGN PATENT DOCUMENTS

WO   WO 01/19288   3/2001

* cited by examiner

*Primary Examiner*—David J. Isabella
(74) *Attorney, Agent, or Firm*—McGlew and Tuttle, P.C.

(57) ABSTRACT

An accommodative intracapsular implant comprises a central optical part and at least two haptic arms (3, 4), the free ends (5, 6) of which are embodied to cooperate with parts of the equatorial zone of the capsular bag, wherein the optical part is formed by joining two elastically-deformable bodies, one body being formed as an envelope (1) and the other body being formed as a core (2).

9 Claims, 1 Drawing Sheet

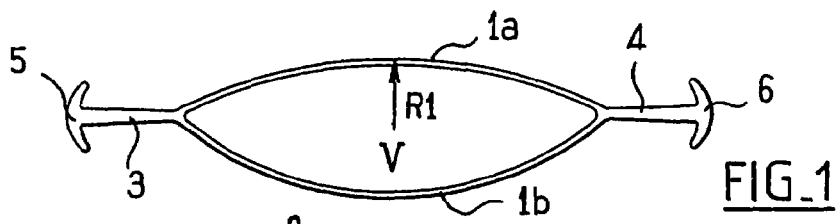
FIG.1
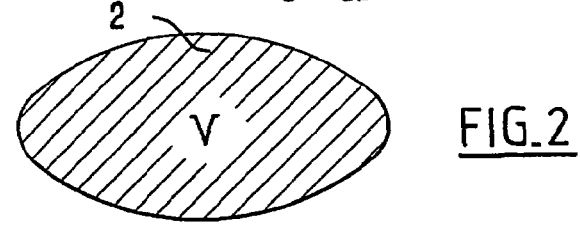
FIG.2
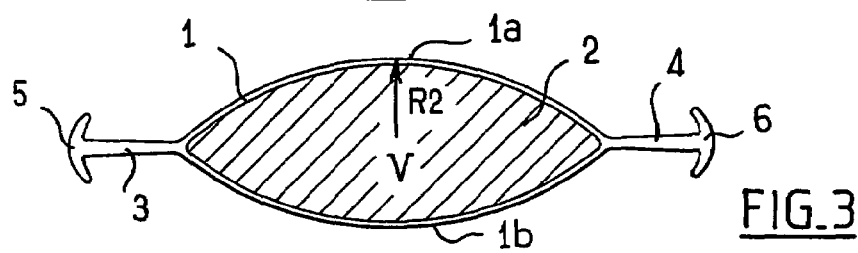
FIG.3
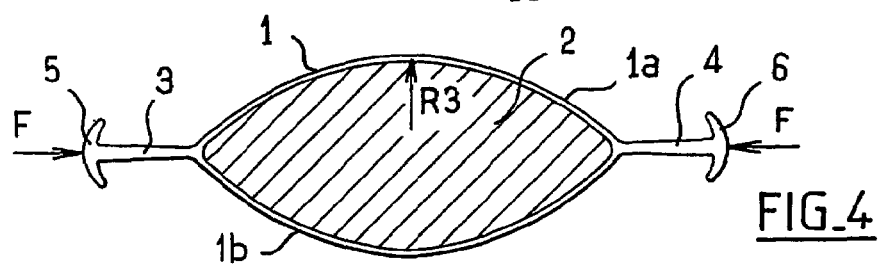
FIG.4
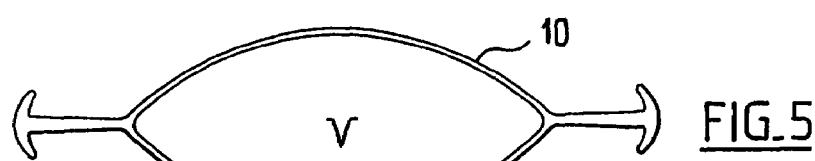
FIG.5
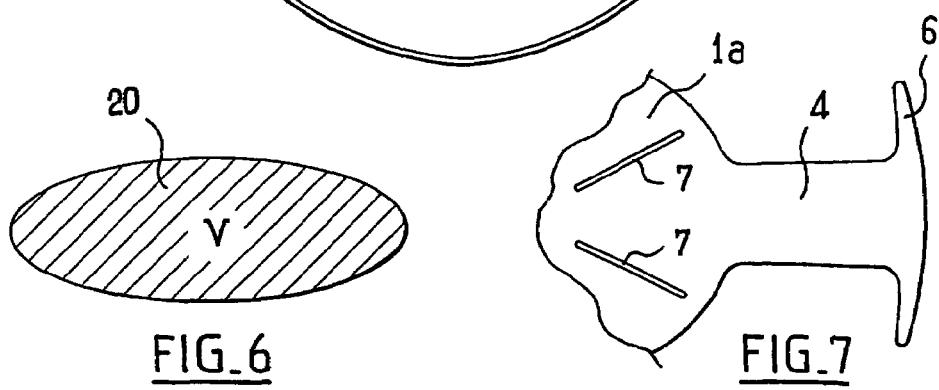
FIG.6
FIG.7

INTRACAPSULAR ACCOMODATIVE IMPLANTS

The replacement of the natural crystalline lens by an artificial crystalline lens (implant) is nowadays usually practiced, in particular on subjects reached of cataract.

The surgery more practiced consists in withdrawing the matter of the natural crystalline lens contained in the capsular bag while preserving the integrity of this bag (except to the central part of its anterior wall) which then remains the receptacle of the implant located therein to replace the withdrawn natural matter.

BACKGROUND OF THE INVENTION

There are now many implants. Most of them allow about recovering a far vision without accommodation possibility for a near vision.

Natural accommodation has made the subject of many studies with the aim to understand the phenomena which are involved to try to transpose them to the implants. The role of the capsular bag in the accommodation is extremely significant, in particular as an element of transmission to the crystalline matter of the forces generated by the ciliary muscle in the one or the other of its relaxed or contracted states, to which the capsular bag is connected by the zonular fibers.

Most recent work to date on the accommodative intracapsular lenses showed that the capsular bag and the crystalline matter are provided with their own elasticity which give the natural crystalline lens a modifiable form depending on the balance of forces between the state of tension of the zonular fibers, the elasticity of the capsular bag and the elasticity of the crystalline matter.

The loss of the accommodative capacity seems to be the result of an alteration of the module of elasticity of the crystalline matter in the course of the time, which opposes an increasingly large resistance to the force of the bag for finally solidifying in an invariable state (regarding the forces brought into play) close to its shape for the far vision. This is the phenomenon of presbyopia.

OBJECT OF THE INVENTION

One of the objects of the invention is to propose an accommodative intracapsular implant which reproduces the natural mechanisms brought into play at the time of the accommodation.

BRIEF DESCRIPTION OF THE INVENTION

To this end the invention relates to an accommodative implant including a central optical part and at least two haptic arms whose loose ends are formed to co-operate with portions of the equatorial zone of the capsular bag, characterized in that the optical part is formed by two bodies elastically deformable joined together, one shaped as an envelope and the other in the shape of core, said envelope having an external surface with a convex anterior face which has, when the envelope is empty, a first radius of curvature and when the core is housed in the envelope, a second radius of curvature different from the first radius of curvature.

It is thus reproduced, in the optical part of the implant an elastic structure in which two fields of antagonistic forces reign which give to the structure a determined shape when the forces are balanced. A disturbance of this balance by the addition of external forces results in a change of the shape of the optical part, in particular of the curve of its anterior face and thus of its optical power. The external forces are the ones transmitted to said composite optical part by the haptic parts which are themselves subjected to the change of the shape of the equatorial zone of the capsular bag. The implant accommodates primarily by a shape change of the optical part (with also a displacement of this one along the optical axis of the eye) contrary to all the known implants which accommodate only by displacement.

BRIEF DESCRIPTION OF THE DRAWINGS

Other characteristics of the invention will appear in the description given hereafter as an example of one embodiment.

It will be referred to the annexed drawings in which:

FIG. 1 is a diametrical cross section of the envelope of the implant according to the invention, FIG. 2 is a diametrical cross section of the core of the implant according to the invention, FIG. 3 is a diametrical cross section of the implant according to the invention, the envelope housing the core, FIG. 4 is a diametrical cut of the implant in its configuration corresponding in an accommodated state, FIGS. 5 and 6 illustrate an alternative embodiment of FIGS. 1 and 2, FIG. 7 is a partial top view of the implant according to the invention.

The implant includes two parts: an envelope 1 represented empty on FIG. 1 and a core 2 represented in its free state on FIG. 2. The envelope 1 forms a hull made of elastic material, provided with two radial arms 3 and 4 equipped with end soles 5 and 6. This is the haptic part of the implant which engages equatorial zones of the capsular bag of the eye which is not represented.

Interior volume V of hull 1 is identical to volume V of core 2. This core 2 is carried out in an elastomer material, therefore elastically deformable so that when introduced into hull 2 this latter is inflated by the core and the core is flattened by the hull, because the free shape of the core 2 is more convex than the shape of volume V of the hull. The final shape reached by the optical part of the implant (that constitutes volume V of the hull filled with the core 2) is represented on FIG. 3.

Interior volume of the hull may be slightly greater than the one of the core made of elastomeric material in as much as this volume in excess has no significant influence on the mutual action of the hull and the core when assembled. The location of the core into the hull is made by any appropriate means: injection through an equatorial slit of the hull, junction of two half hulls around the core . . . .

In this shape, the radius of curvature R2 of the anterior face 1a of hull 1 is different from this same radius R1 when the hull is empty. Here the R2 radius is smaller than the radius R1. The shape reached on FIG. 3 is the result of the balance of two fields of antagonistic forces born from the elastic compression of core 2 by hull 1 and from elastic expansion of hull 1 by core 2.

By causing an alteration of this balance by an external field of forces F (see FIG. 4) one modifies the balance, therefore the shape, of the optical part of the implant, therefore the radius of curvature R3 of its anterior face 1a is modified. The optical power of the composite lens 1, 2 is thus modified.

In the case of FIG. 4, the field of forces F results from the action of the capsular bag on soles 5 and 6 when the zonular fibers are relaxed and that, by natural elasticity, the bag contracts radially. This is the state of the implant for near vision, the radius R3 being smaller than the radius R2 which corresponds to the shape of the lens for a far vision.

Of course the posterior face 1b of hull 1 has its radius of curvature changing as a result of the modification of the balance of the forces. It is possible, for example, by means of using various thicknesses of the hull wall 1, to influence such or such deformation, anterior or posterior, or even such type of deformation (spherical, conical . . . ). FIG. 7 shows slits 7 provided in the anterior wall of the hull 1 to illustrate means of adjustment of the ability of this hull to become deformed.

On FIGS. 5 and 6, the shown embodiment illustrates a hull 10 which, empty, has a volume V more convex than that of core 20 to be housed. This difference in shapes generates, like previously, fields of forces, the balance of which results in the intermediate shape of the core housed in the hull.

Core 2, 20 can be made of a non elastic colloidal material (gel) housed in an envelope or an elastic pocket which confers to him its shape and its capacity with being elastically deformed.

What is claimed is:

1. An accommodative intracapsular implant comprising:
   a central optical part; and
   at least two haptic arms (3,4), free ends (5,6) of which are formed to cooperate with portions of equatorial zones of a capsular bag,
   wherein said optical part is formed by two bodies, elastically deformable and joined together, wherein:
   one body is shaped as an envelope (I), having an interior volume (V) and with an envelope initial free shape, and
   the other body is shaped as a core (2), having a volume (V) and a core initial free shape,
   the interior volume (V) of the envelope (1) is identical to the volume (V) of the core (2),
   the core initial free shape is more convex than the envelope initial free shape, such that the core (2), when introduced into the envelope (I), is flattened by the envelope (1),
   the envelope (1) has an external surface with a convex anterior face (1a) which has,
   when the envelope (1) is empty, a first radius of curvature (R1), and
   when the envelope (1) houses the core (2), a second radius of curvature (R2),
   said second radius of curvature (R2) being smaller than said first radius of curvature (R1), and
   when the envelope (I) houses the core (2) and a field of forces (F) resulting from a radial contraction of the capsular bag is applied to the free ends (5, 6) of the haptic arms (3, 4), a third radius of curvature (R3), said third radius of curvature (R3) being smaller than said second radius of curvature (R2), thus resulting in a change of the optical power of the optical part.

2. An implant according to claim 1, wherein the interior volume (V) of the envelope (1) is identical to the volume (V) of the core (2) with the envelope initial free shape being different from the core initial free shape, when the envelope (1) and the core (2) are in a free state with the core not inserted into the envelope.

3. An implant according to claim 1, wherein the core (2) is made of an elastomeric material defining the initial free shape of the core.

4. An implant according to claim 1, wherein the anterior wall of the envelope is provided with at least one radial slit (7).

5. An accommodative intracapsular implant comprising:
   a central optical part;
   two haptic arms (3, 4) with respective free ends (5,6) for cooperation with portions of equatorial zones of a capsular bag,
   wherein said optical part is formed by two bodies, elastically deformable and joined together and
   one body is shaped as an envelope (I), having an interior volume (V) and an envelope initial free shape, and
   the other body is shaped as a core (2), having a volume (V) and an core initial free shape,
   the interior volume (V) of the envelope (1) is greater than the volume (V) of the core (2),
   the core initial free shape is more convex than the shape of the volume (V) of the envelope (1), such that the core (2), when introduced into the envelope (I), is flattened by the envelope (1),
   the envelope (1) has an external surface with a convex anterior face (1a) which has,
   when the envelope (1) is empty, a first radius of curvature (Ri), and
   when the envelope (1) houses the core (2), a second radius of curvature (R2),
   said second radius of curvature (R2) being smaller than said first radius of curvature (R 1),
   when the envelope (1) houses the core (2) and a field of forces resulting from the radial contraction of the capsular bag is applied to the free ends (5,6) of the haptic arms (3,4), a third radius of curvature (R3), said third radius of curvature (R3) being smaller than said second radius of curvature (R2), thus resulting in a change of the optical power of the optical part.

6. An accommodative intracapsular implant comprising:
   an elastically deformable envelope body having an empty interior volume and having an envelope body empty initial shape with anterior face with an empty initial shape radius of curvature and having two haptic arms with respective free ends for cooperation with portions of equatorial zones of a capsular bag; and
   an elastically deformable core body having a non-inserted core body initial volume and a non-inserted core body initial shape that is more convex than said envelope body empty initial shape, said core body being inserted into said envelope body to form a central optical part having an equilibrium shape differing from said envelope body empty initial shape and differing from said non-inserted core body initial shape, said envelope body exerting a pre-compression/tension on said core body to bias said core body toward a flatter shape than said core body initial shape and said core body exerting a pre-compression/tension on said envelope body to bias said envelope body toward a more convex shape than said envelope body initial shape, said anterior face of said envelope body, in said equilibrium shape, having an equilibrium shape radius of curvature that is smaller than said empty initial shape radius of curvature, and whereby upon a field of forces, resulting from the radial contraction of the capsular bag, being applied to said free ends, said forces at least partially counteracting or acting with said envelope body exerting a pre-compression/tension on said core body and said forces at least partially counteracting or acting with said core body exerting a pre-compression/tension on said envelope body to change from said equilibrium shape to an applied force shape having an applied force shape radius of curvature that is different from said empty initial shape radius of curvature, thus resulting in a change of the optical power of the optical part.

7. An implant according to claim 6, wherein said empty interior volume of said envelope body is substantially the same as said non-inserted core body initial volume.

8. An implant according to claim 6, wherein said empty interior volume of said envelope body is larger than said non-inserted core body initial volume.

9. An implant according to claim 6, wherein said anterior wall of the envelope is provided with at least one radial slit.

* * * * *